(12) United States Patent
Syverson et al.

(10) Patent No.: US 7,258,867 B2
(45) Date of Patent: *Aug. 21, 2007

(54) AROMATIC COMPOSITIONS AS INHIBITORS OF EXOPROTEIN PRODUCTION IN NON-ABSORBENT ARTICLES

(75) Inventors: Rae Ellen Syverson, Fond du Lac, WI (US); Richard A. Proctor, Madison, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 149 days.

This patent is subject to a terminal disclaimer.

(21) Appl. No.: 10/803,345

(22) Filed: Mar. 18, 2004

(65) Prior Publication Data
US 2004/0197371 A1   Oct. 7, 2004

Related U.S. Application Data

(62) Division of application No. 09/969,391, filed on Oct. 2, 2001.

(51) Int. Cl.
*A61F 9/00* (2006.01)
*A61F 13/15* (2006.01)
*A01N 25/34* (2006.01)

(52) U.S. Cl. ............... 424/400; 424/402; 424/404; 604/360

(58) Field of Classification Search ......... 424/400, 424/402, 404; 604/360
See application file for complete search history.

(56) References Cited

U.S. PATENT DOCUMENTS

| | | | |
|---|---|---|---|
| 3,317,376 A | 5/1967 | Schattner | |
| 4,339,462 A | 7/1982 | Muntwyler et al. | |
| 4,405,323 A | 9/1983 | Auerbach | |
| 4,413,032 A | 11/1983 | Hartmann et al. | |
| 4,413,986 A | 11/1983 | Jacobs | |
| 4,424,054 A | 1/1984 | Conn et al. | |
| 4,431,427 A | 2/1984 | Lefren et al. | |
| 4,470,978 A | 9/1984 | Stolar | |
| 4,560,549 A * | 12/1985 | Ritchey | 424/431 |
| 4,582,717 A | 4/1986 | von Bittera et al. | |
| 4,585,792 A | 4/1986 | Jacob et al. | |
| 4,722,936 A | 2/1988 | Jacob | |
| 4,722,937 A | 2/1988 | Jacob et al. | |
| 4,769,021 A | 9/1988 | Kass | |
| 4,952,211 A | 8/1990 | Snider | |
| 5,000,749 A | 3/1991 | LeVeen et al. | |
| 5,070,889 A | 12/1991 | Leveen et al. | |
| 5,071,648 A | 12/1991 | Rosenblatt | |
| 5,156,164 A | 10/1992 | Leveen et al. | |
| 5,180,749 A | 1/1993 | Cusack et al. | |
| 5,221,693 A | 6/1993 | Shetty | |
| 5,342,331 A | 8/1994 | Silber et al. | |
| 5,389,374 A | 2/1995 | Brown-Skrobot | |
| 5,476,455 A | 12/1995 | Silber | |

(Continued)

FOREIGN PATENT DOCUMENTS

DE  1204777  * 11/1965

(Continued)

OTHER PUBLICATIONS

Matsumura et al., Surface Activities, Biodegradability and Antimircobial Properties of n-Alkyl Glucosides, Mannosides and Galactosides, *J. Amer. Oil Chem. Soc.*, Dec. 1990, pp. 996-1000, vol. 67.

(Continued)

*Primary Examiner*—Lakshmi S. Channavajjala
(74) *Attorney, Agent, or Firm*—Senniger Powers

(57) ABSTRACT

Non-absorbent articles are disclosed. The non-absorbent articles include an effective amount of an aromatic inhibitory compound to substantially inhibit the production of exotoxins by Gram positive bacteria. The aromatic inhibitory compounds of the present invention have the general formula:

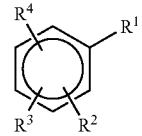

wherein $R^1$ is selected from the group consisting of H,

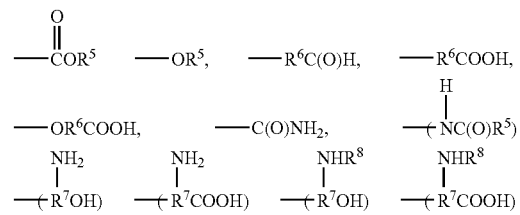

and $NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —C(O)$R^9$; $R^9$ is hydrogen or a monovalent saturated or unsaturated aliphatic hydrocarbyl moiety.

20 Claims, No Drawings

U.S. PATENT DOCUMENTS

| | | |
|---|---|---|
| 5,498,252 A | 3/1996 | Silber |
| 5,527,892 A | 6/1996 | Borsotti et al. |
| 5,540,979 A | 7/1996 | Yahiaoui et al. |
| 5,547,985 A | 8/1996 | Brown-Skrobot et al. |
| 5,601,814 A | 2/1997 | Barton et al. |
| 5,612,045 A | 3/1997 | Syverson |
| 5,618,554 A | 4/1997 | Syverson |
| 5,641,503 A | 6/1997 | Brown-Skrobot |
| 5,679,369 A | 10/1997 | Brown-Skrobot |
| 5,685,872 A | 11/1997 | Syverson |
| 5,705,182 A | 1/1998 | Brown-Skrobot |
| 5,719,113 A | 2/1998 | Fendler et al. |
| 5,728,690 A | 3/1998 | Chen |
| 5,753,252 A | 5/1998 | Brown-Skrobot |
| 5,770,543 A | 6/1998 | Garst et al. |
| 5,814,567 A | 9/1998 | Yahiaoui et al. |
| 5,817,047 A | 10/1998 | Osborn, III et al. |
| 5,895,643 A | 4/1999 | Hoppe et al. |
| 5,898,030 A | 4/1999 | Samaritani |
| 5,932,495 A | 8/1999 | Boney et al. |
| 5,945,175 A | 8/1999 | Yahiaoui et al. |
| 6,017,832 A | 1/2000 | Yahiaoui et al. |
| 6,028,016 A | 2/2000 | Yahiaoui et al. |
| 6,039,716 A | 3/2000 | Jessup et al. |
| 6,060,636 A | 5/2000 | Yahiaoui et al. |
| 6,107,268 A | 8/2000 | Yahiaoui et al. |
| 6,159,924 A | 12/2000 | Weller et al. |
| 6,224,886 B1 | 5/2001 | Charlton et al. |
| 6,231,557 B1 | 5/2001 | Krautkramer et al. |
| 6,281,999 B1 | 8/2001 | Watson et al. |
| 6,294,186 B1 | 9/2001 | Beerse et al. |
| 6,416,779 B1 | 7/2002 | D'Augustine et al. |
| 6,767,508 B1 * | 7/2004 | Yahiaoui et al. ............... 422/28 |
| 6,821,999 B2 * | 11/2004 | Syverson et al. ............ 514/438 |

FOREIGN PATENT DOCUMENTS

| | | |
|---|---|---|
| EP | 0 009 977 A1 | 4/1980 |
| EP | 0 053 221 A2 | 6/1982 |
| EP | 0 110 793 B1 | 6/1984 |
| EP | 0 391 741 A2 | 10/1990 |
| EP | 0 395 099 A2 | 10/1990 |
| EP | 0 483 812 B1 | 5/1992 |
| EP | 0 483 835 A1 | 5/1992 |
| EP | 0 683 260 A2 | 2/1995 |
| GB | 1068667 | 5/1967 |
| GB | 2186486 A | 8/1987 |
| WO | WO87/03208 A1 | 6/1987 |
| WO | WO94/22501 A1 | 10/1994 |
| WO | WO96/40300 A2 | 12/1996 |
| WO | WO98/09662 A1 | 3/1998 |
| WO | WO98/41179 A1 | 9/1998 |
| WO | WO99/12505 A2 | 3/1999 |
| WO | WO99/38541 A1 | 8/1999 |
| WO | WO99/61079 A1 | 12/1999 |

OTHER PUBLICATIONS

PCT/US02/28756 PCT International Search Report dated Dec. 18, 2002.

Osol, A., et al. (eds.), Remington's Pharmaceutical Sciences, 16th Edition, 1980, pp. 999, Philadelphia College of Pharmacy and Science.

* cited by examiner

AROMATIC COMPOSITIONS AS INHIBITORS OF EXOPROTEIN PRODUCTION IN NON-ABSORBENT ARTICLES

CROSS-REFERENCE TO RELATED APPLICATION

This divisional patent application claims priority from U.S. patent application Ser. No. 09/969,391 filed on Oct. 2, 2001, the entirety of which is hereby incorporated by reference.

BACKGROUND OF THE INVENTION

The present invention relates to the inhibition of exoprotein production in association with a non-absorbent article. More particularly, the present invention relates to the coating or treatment of certain aromatic compounds onto non-absorbent articles and the effects of these compounds on Gram positive bacteria.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal fluid. The bacterial flora of the vagina is comprised of both aerobic and anaerobic bacteria. The more commonly isolated bacteria are *Lactobacillus* species, *Corynebacteria, Gardnerella vaginalis, Staphylococcus* species, *Peptococcus* species, *aerobic* and *anaerobic Streptococcus* species, and *Bacteroides* species. Other microorganisms that have been isolated from the vagina on occasion include yeast (*Candida albicans*), *protozoa* (*Trichomonas vaginalis*), *mycoplasma* (*Mycoplasma hominis*), *chlamydia* (*Chlamydia trachomatis*), and viruses (*Herpes simplex*). These latter organisms are generally associated with vaginitis or venereal disease, although they may be present in low numbers without causing symptoms.

Physiological, social, and idiosyncratic factors effect the quantity and species of bacteria present in the vagina. Physiological factors include age, day of the menstrual cycle, and pregnancy. For example, vaginal flora present in the vagina throughout the menstrual cycle can include *lactobacilli, corynebacterium, ureaplasma*, and *mycoplasma*. Social and idiosyncratic factors include method of birth control, sexual practices, systemic disease (e.g., diabetes), and medications.

Bacterial proteins and metabolic products produced in the vagina can effect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of *lactobacilli* and their production of acidic products. Microorganisms in the vagina can also produce antimicrobial compounds such as hydrogen peroxide and bactericides directed at other bacterial species. One example is the lactocins, bacteriocin-like products of *lactobacilli* directed against other species of *lactobacilli*.

Some microbial products produced in the vagina may negatively affect the human host. For example, *S. aureus* can produce and excrete into its environment a variety of exoproteins including enterotoxins, Toxic Shock Syndrome Toxin-1 (TSST-1), and enzymes such as proteases and lipase. When absorbed into the bloodstream of the host, TSST-1 may produce Toxic Shock Syndrome (TSS) in non-immune humans.

*S. aureus* is found in the vagina of approximately 16% of healthy women of menstrual age. Approximately 25% of the *S. aureus* isolated from the vagina are found to produce TSST-1. TSST-1 and some of the *staphylococcal enterotoxins* have been identified as causing TSS in humans.

Symptoms of Toxic Shock Syndrome generally include fever, diarrhea, vomiting and a rash followed by a rapid drop in blood pressure. Multiple organ failure occurs in approximately 6% of those who contract the disease. *S. aureus* does not initiate Toxic Shock Syndrome as a result of the invasion of the microorganism into the vaginal cavity. Instead as *S. aureus* grows and multiplies, it can produce TSST-1. Only after entering the bloodstream does TSST-1 toxin act systemically and produce the symptoms attributed to Toxic Shock Syndrome.

Menstrual fluid has a pH of about 7.3. During menses, the pH of the vagina moves toward neutral and can become slightly alkaline. This change permits microorganisms whose growth is inhibited by an acidic environment the opportunity to proliferate. For example, *S. aureus* is more frequently isolated from vaginal swabs during menstruation than from swabs collected between menstrual periods.

When *S. aureus* is present in an area of the human body that harbors a normal microbial population such as the vagina, it may be difficult to eradicate the *S. aureus* bacterium without harming members of the normal microbial flora required for a healthy vagina. Typically, antibiotics that kill *S. aureus* are not an option for use in products inserted into the vagina because of their effect on the normal vaginal microbial flora and their propensity to stimulate toxin production if all of the *S. aureus* are not killed. An alternative to complete eradication is technology designed to prevent or substantially reduce the bacterium's ability to produce toxins.

There have been numerous attempts to reduce or eliminate pathogenic microorganisms and menstrually occurring Toxic Shock Syndrome by incorporating one or more biostatic, biocidal, and/or detoxifying compounds into vaginal products. For example, L-ascorbic acid has been applied to a menstrual tampon to detoxify toxin found in the vagina. Others have incorporated monoesters and diesters of polyhydric aliphatic alcohols, such as glycerol monolaurate, as biocidal compounds (see, e.g., U.S. Pat. No. 5,679,369). Still others have introduced other non-ionic surfactants, such as alkyl ethers, alkyl amines, and alkyl amides as detoxifying compounds (see, e.g., U.S. Pat. Nos. 5,685,872, 5,618,554, and 5,612,045).

Despite the aforementioned art, there continues to be a need for compounds that will effectively inhibit the production of exoproteins, such as TSST-1, from Gram positive bacteria, and maintain activity even in the presence of the enzymes lipase and esterase which can have adverse effects on potency and which may also be present in the vagina. Further, it is desirable that the detoxifying compounds useful in the inhibition of the production of exoproteins be substantially non-harmful to the natural flora found in the vaginal area. It is also desirable that the detoxifying compound be coated or otherwise introduced onto a non-absorbent substrate prior to use.

SUMMARY OF THE INVENTION

The present invention is based on the discovery that when one or more aromatic compounds having the general structure:

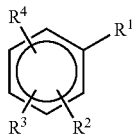

wherein $R^1$ is selected from the group consisting of H,

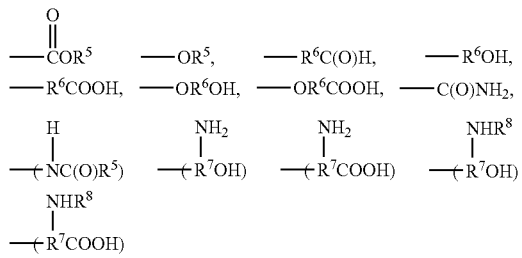

and $NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and $-C(O)R^9$; $R^9$ is hydrogen or a monovalent saturated or unsaturated aliphatic hydrocarbyl moiety, are incorporated onto a non-absorbent substrate, the production of exoprotein in Gram positive bacterium is substantially inhibited.

The present invention relates to non-absorbent substrates or articles which inhibit the production of exoproteins from Gram-positive bacteria. The substrates are particularly useful for inhibiting the production of TSST-1 from *S. aureus* bacteria in the vaginal area. Examples of suitable non-absorbent substrates which can have the aromatic compounds of the present invention incorporated thereon include non-absorbent incontinence devices, barrier birth control devices, douches, contraceptive sponges, and tampon applicators. One specific example of a non-absorbent incontinence device is a female barrier incontinence device, such as an incontinence pledget formed from a resilient material like rubber. Another suitable non-absorbent substrate is the applicator used with a tampon. For example, the tampon applicator may have the aromatic compound coated on an outer surface, such that when the applicator is used to introduce a tampon into a women's vagina the aromatic compound (typically in the form of a cream, wax, gel or other suitable form) is transferred from the applicator onto the wall of the vagina.

It is a general object of the present invention to provide a non-absorbent article which inhibits the production of exoprotein from Gram positive bacterium. A more specific object of the present invention is to provide a non-absorbent incontinence device, a barrier birth control device, a contraceptive sponge, tampon applicator, or a douche incorporating one or more aromatic compounds which act to substantially inhibit the production of TSST-1 and Enterotoxin B by *S. aureus.*

Another object of the present invention is to provide a non-absorbent substrate incorporating one or more aromatic compounds in combination with one or more other inhibitory ingredients such as, but not limited to, for example, laureth-4, PPG-5 lauryl ether, 1-0-dodecyl-rac-glycerol, disodium laureth sulfosuccinate, glycerol monolaurate, alkylpolyglycosides, polyethylene oxide (2) sorbital ether or myreth-3-myristate which in combination act to substantially inhibit the production of TSST-1 and Enterotoxin B by *S. aureus*.

A further object of the present invention is to provide a non-absorbent substrate that has incorporated therewith one or more compounds that will inhibit the production of exoproteins from Gram positive bacterium without significantly imbalancing the natural flora present in the vaginal tract.

Other objects and advantages of the present invention, and modifications thereof, will become apparent to persons skilled in the art without departure from the inventive concepts defined in the claims.

DETAILED DESCRIPTION OF THE PREFERRED EMBODIMENTS

In accordance with the present invention, it has been discovered that aromatic compounds as described herein can be used in combination with non-absorbent articles, such as incontinence devices, for example, to substantially inhibit the production of exoproteins, such as TSST-1, from Gram positive bacteria. It has also been discovered that the aromatic compounds can also be used in combination with surface-active agents such as, for example, compounds with an ether, ester, amide, glycosidic, or amine bond linking a $C_8$-$C_{18}$ fatty acid to an aliphatic alcohol, polyalkoxylated sulfate salt, or polyalkoxylated sulfosuccinic salt, to substantially inhibit the production of exoproteins such as TSST-1 from Gram positive bacteria.

This invention will be described herein in detail in connection with various non-absorbent substrates or products such as non-absorbent incontinence devices, barrier birth control devices, contraceptive sponges, tampon applicators, and douches, but will be understood by persons skilled in the art to be applicable to other non-absorbent articles, devices and/or products as well wherein the inhibition of exoproteins from Gram positive bacteria would be beneficial. As used herein, the phrase "non-absorbent article" generally refers to substrates or devices which include an outer layer formed from a substantially hydrophobic material which repels fluids such as menses, blood products and the like. Suitable materials for construction the non-absorbent articles of the present invention include, for example, rubber, plastic, and cardboard.

It has been discovered that certain aromatic compounds can substantially inhibit the production of exoprotein by Gram positive bacterium and, specifically, the production of TSST-1 and Enterotoxin B from *S. aureus* bacterium. The aromatic compounds useful in the present invention have the general chemical structure:

$$\underset{R^3}{\overset{R^4}{\bigcirc}}\overset{R^1}{\underset{R^2}{}}$$

wherein $R^1$ is selected from the group consisting of H, $$-COR^5 \quad -OR^5, \quad -R^6C(O)H, \quad -R^6OH,$$
$$-R^6COOH, \quad -OR^6OH, \quad -OR^6COOH, \quad -C(O)NH_2,$$

$$\underset{-(NC(O)R^5)}{\overset{H}{|}} \quad \underset{-(R^7OH)}{\overset{NH_2}{|}} \quad \underset{-(R^7COOH)}{\overset{NH_2}{|}} \quad \underset{-(R^7OH)}{\overset{NHR^8}{|}}$$

$$\underset{-(R^7COOH)}{\overset{NHR^8}{|}}$$

and $NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is hydrogen or a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —C(O)$R^9$; $R^9$ is a monovalent saturated or unsaturated aliphatic hydrocarbyl moiety.

The hydrocarbyl moieties described herein include both straight chain and branched chain hydrocarbyl moieties and may or may not be substituted and/or interrupted with hetero atoms. Desirably, the aromatic compounds for use in the present invention contain at least one OH and/or COOH group. The OH and/or COOH group can be bonded to the aromatic structure, or can be bonded to an atom which may or may not be directly bonded to the aromatic structure. $R^5$ is desirably a monovalent saturated aliphatic hydrocarbyl moiety having from 1 to about 15 carbon atoms, desirably from 1 to about 14 carbon atoms. $R^6$ is desirably a divalent saturated or unsaturated aliphatic hydrocarbyl moiety having from 1 to about 15 carbon atoms, desirably from 1 to about 14 carbon atoms. $R^7$ is desirably a trivalent saturated or unsaturated aliphatic hydrocarbyl moiety having from 1 to about 15 carbon atoms, desirably from 1 to about 10 carbon atoms, and more desirably from 1 to about 4 carbon atoms. Hetero atoms which can interrupt the hydrocarbyl moiety include, for example, oxygen and sulfur.

Preferred aromatic compounds of the present invention include 2-phenylethanol, benzyl alcohol, trans-cinnamic acid, 4-hydroxybenzoic acid, methyl ester, 2-hydroxybenzoic acid, 2-hydoxybenzamide, acetyl tyrosine, 3,4,5-trihydroxybenzoic acid, lauryl 3,4,5-trihydroxybenzoate, phenoxyethanol, 4-hydroxy-3-methoxybenzoic acid, p-aminobenzoic acid, and 4-acetamidophenol.

In accordance with the present invention, the non-absorbent article including the aromatic compound contains an effective amount of the inhibiting aromatic compound to substantially inhibit the formation of TSST-1 when the non-absorbent article or inhibiting compound thereon is exposed to *S. aureus* bacteria. Several methods are known in the art for testing the effectiveness of potential inhibitory agents on the inhibition of the production of TSST-1 in the presence of *S. aureus*. One such preferred method is set forth in Example 1 below. When tested in accordance with the testing methodology described herein, desirably, the inhibiting aromatic compounds reduce the formation of TSST-1 when the non-absorbent article is exposed to *S. aureus* by at least about 40%, more desirably by at least about 50%, still more desirably by at least about 60%, still more desirably by at least about 70%, still more desirably by at least about 80%, still more desirably by at least about 90%, and still more desirably by at least about 95%.

Effective amounts of aromatic compound that significantly reduce the production of TSST-1 have been found to be at least about 0.1 micromoles of the aromatic compound per gram of the non-absorbent product. Desirably, the aromatic compound ranges from about 0.5 micromoles per gram of non-absorbent to about 100 micromoles per gram of non-absorbent and more desirably from about 1.0 micromoles per gram of non-absorbent to about 50 micromoles per gram of non-absorbent. Although "aromatic compound" is used in the singular, one skilled in the art would understand that it includes the plural, and that various aromatic compounds within the scope of this invention may be used in combination.

The aromatic compounds of the present invention can be prepared and applied to the non-absorbent article in any suitable form, but are typically prepared in forms including, without limitation, aqueous solutions, lotions, balms, gels, salves, ointments, boluses, suppositories, and the like. One skilled in the art would recognize that other forms may perform equally well.

The aromatic compounds may be applied to the non-absorbent article using conventional methods for applying an inhibitory agent to the desired non-absorbent article. For example, non-absorbent articles may be dipped directly into a liquid bath having the inhibitory compound and then can be air dried, if necessary, to remove any volatile solvents. Alternatively, the non-absorbent articles of the present invention can be sprayed or otherwise coated with the inhibitory aromatic compounds of the present invention.

The substantially inhibitory aromatic compounds may additionally employ one or more conventional pharmaceutically-acceptable and compatible carrier materials useful for the desired application. The carrier can be capable of co-dissolving or suspending the materials used on the non-absorbent article. Carrier materials suitable for use in the instant invention include those well-known for use in the cosmetic and medical arts as a basis for ointments, lotions, creams, salves, aerosols, suppositories, gels, and the like. For example, the aromatic compound can be formulated into a variety of formulation such as those employed in current commercial douche formulations, or in higher viscosity douches.

The aromatic compounds of the present invention may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

In another embodiment of the present invention, the inhibitory aromatic compounds described above can be used in combination with one or more surface active agents to reduce the production of TSST-1 without significantly eliminating the beneficial bacterial flora. The surface active agents can include, for example, compounds with an ether, ester, amide, glycosidic, or amine bond linking a $C_8$-$C_{18}$ fatty acid to an aliphatic alcohol, polyalkoxylated sulfate salt, or polyalkoxylated sulfosuccinic salt.

In one embodiment, the inhibitory aromatic compounds described herein can be used in combination with ether compounds having the general formula:

$$R^{10}-O-R^{11}$$

wherein $R^{10}$ is a straight or branched alkyl or alkenyl group having a chain of from about 8 to about 18 carbon atoms and $R^{11}$ is selected from an alcohol, a polyalkoxylated sulfate salt or a polyalkoxylated sulfosuccinate salt.

The alkyl, or the $R^{10}$ moiety of the ether compounds useful for use in combination with the inhibitory aromatic compounds described herein, can be obtained from saturated and unsaturated fatty acid compounds. Suitable compounds include, $C_8$-$C_{18}$ fatty acids, and preferably, fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic acids.

Preferred unsaturated fatty acids are those having one or two cis-type double bonds and mixtures of these materials. Suitable materials include myrystoleic, palmitoleic, linolenic and mixtures thereof.

Desirably, the $R^{11}$ moiety is an aliphatic alcohol which can be ethoxylated or propoxylated for use in the ether compositions in combination with the inhibitory aromatic compounds described herein. Suitable aliphatic alcohols include glycerol, sucrose, glucose, sorbitol and sorbitan. Preferred ethoxylated and propoxylated alcohols include glycols such as ethylene glycol, propylene glycol, polyethylene glycol and polypropylene glycol.

The aliphatic alcohols can be ethoxylated or propoxylated by conventional ethoxylating or propoxylating compounds and techniques. The compounds are preferably selected from the group consisting of ethylene oxide, propylene oxide, and mixtures thereof, and similar ringed compounds which provide a material which is effective.

The $R^{11}$ moiety can further include polyalkoxylated sulfate and polyalkoxylated sulfosuccinate salts. The salts can have one or more cations. Preferably, the cations are sodium, potassium or both.

Preferred ether compounds for use in combination with the inhibitory aromatic compounds described herein include laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate, and polyethylene oxide (2) sorbitol ether.

In accordance with the present invention, the non-absorbent article contains an effective amount of the combination of the inhibitory aromatic and ether compounds. The amount of ether compound introduced onto the non-absorbent article is at least about 0.0001 millimoles of ether compound per gram of non-absorbent article, and desirably at least about 0.005 millimoles of ether compound per gram of non-absorbent article. In a preferred embodiment, the non-absorbent article contains from about 0.005 millimoles of ether compound per gram of non-absorbent article to about 2 millimoles of ether compound per gram of non-absorbent article.

The non-absorbent articles of the present invention containing a combination of two active ingredients can be a variety of non-absorbent articles including, for example, incontinence devices, barrier birth control devices, contraceptive sponges, douches, tampon applicators, and the like.

The non-absorbent articles of the present invention containing a first inhibitory aromatic compound and a second inhibitory ether compound contain a sufficient amount of both inhibitory compounds to substantially inhibit the formation of TSST-1 when the non-absorbent article is exposed to S. aureus bacteria. Desirably, the combination of inhibitory compounds reduces the formation of TSST-1 when the non-absorbent article is exposed to S. aureus by at least about 40%, more desirably at least about 50%, still more desirably at least about 60%, still more desirably by at least about 70%, still more desirably by at least about 80%, still more desirably by at least about 90%, and still more desirably by at least about 95%.

The non-absorbent articles of the present invention containing the combination of aromatic inhibitory compounds and ether inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitical agents, antipruritics, astringents, local anaesthetics, or anti-inflammatory agents.

Typically, the non-absorbent article will contain a molar ratio of inhibitory aromatic compound to ether compound of from about 1:6 to about 1:0.05.

In another embodiment, the inhibitory aromatic compounds described herein can be used in combination with an alkyl polyglycoside compound. Suitable alkyl polyglycosides for use in combination with the inhibitory aromatic compounds include alkyl polyglycosides having the general formula:

$$H-(Z_n)-O-R^{14}$$

wherein Z is a saccharide residue having 5 or 6 carbon atoms, n is a whole number from 1 to 6, and $R^{14}$ is a linear or branched alkyl group having from about 8 to about 18 carbon atoms. Commercially available examples of suitable alkyl polyglycosides having differing carbon chain lengths include Glucopon 220, 225, 425, 600, and 625, all available from Henkel Corporation (Ambler, Pa.). These products are all mixtures of alkyl mono- and oligoglucopyranosides with differing alkyl group chain lengths based on fatty alcohols derived from coconut and/or palm kernel oil. Glucopon 220, 225, and 425 are examples of particularly suitable alkyl polyglycosides for use in combination with the inhibitory aromatic compounds of the present invention. Another example of a suitable commercially available alkyl polyglycoside is TL 2141, a Glucopon 220 analog available from ICI Surfactants (Wilmington, Del.).

It should be understood that as referred to herein, an alkylpolyglycoside may consist of a single type of alkyl polyglycoside molecule or, as is typically the case, may include a mixture of different alkyl polyglycoside molecules. The different alkyl polyglycoside molecules may be isomeric and/or may be alkyl polyglycoside molecules with differing alkyl group and/or saccharide portions. By use of the term alkyl poyglycoside isomers reference is made to alkyl polyglycosides which, although including the same alky ether residues, may vary with respect to the location of the alkyl ether residue in the alkyl polyglycoside as well as isomers which differ with respect to the orientation of the functional groups about one or more chiral centers in the molecules. For example, an alkyl polyglycoside can include a mixture of molecules with saccharide portions which are mono, di-, or oligosaccharides derived from more than one 6 carbon saccharide residue and where the mono-, di- or oligosaccharide has been etherified by reaction with a mixture of fatty alcohols of varying carbon chain length. The present alkyl polyglycosides desirably include alkyl groups where the average number of carbon atoms in the alkyl chain is about 8 to about 12. One example of a suitable alkyl polyglycoside is a mixture of alkyl polyglycoside molecules with alkyl chains having from about 8 to about 10 carbon atoms.

The alkyl polyglycosides employed in the non-absorbent articles in combination with the inhibiting aromatic compounds can be characterized in terms of their hydrophilic lipophilic balance (HLB). This can be calculated based on their chemical structure using techniques well known to those skilled in the art. The HLB of the alkyl polyglycosides used in the present invention typically falls within the range of about 10 to about 15. Desirably, the present alkyl polyglycosides have an HLB of at least about 12 and, more desirably, about 12 to about 14.

In accordance with the present invention, the non-absorbent article contains an effective amount of the combination of the inhibitory aromatic and alkyl polyglycoside compounds. The amount of alkyl polyglycoside compound included in the non-absorbent article is at least about 0.0001 millimoles of alkyl polyglycoside per gram of non-absorbent article, and desirably at least about 0.005 millimoles of alkyl polyglycoside per gram of non-absorbent article. In a preferred embodiment, the non-absorbent article contains from about 0.005 millimoles per gram of non-absorbent article to about 2 millimoles per gram of non-absorbent article.

The non-absorbent articles of the present invention containing a combination of inhibitory or active ingredients such as aromatic inhibitory compounds and alkyl polyglycoside inhibitory compounds can be a variety of non-absorbent articles including, for example, incontinence devices, barrier birth control devices, contraceptive sponges, douches, tampon applicators, and the like.

The non-absorbent articles of the present invention containing a first inhibitory aromatic compound and a second inhibitory alkyl polyglycoside compound contain a sufficient amount of both inhibitory compounds to substantially inhibit the formation of TSST-1 when the non-absorbent article is exposed to *S. aureus* bacteria. Desirably, the combination of inhibitory compounds reduces the formation of TSST-1 when the non-absorbent article is exposed to *S. aureus* by at least about 40%, more desirably at least about 50%, still more desirably at least about 60%, still more desirably by at least about 70%, still more desirably by at least about 80%, still more desirably by at least about 90%, and still more desirably by at least about 95%.

The non-absorbent articles of the present invention containing the combination of aromatic inhibitory compounds and alkyl polyglycoside inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

Typically, the non-absorbent article will contain a molar ratio of inhibitory aromatic compound to alkyl glycoside compound of from about 1:1 to about 1:0.05.

In another embodiment, the inhibitory aromatic compounds described herein can be used in combination with an amide containing compound having the general formula:

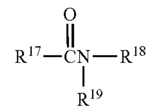

wherein $R^{17}$, inclusive of the carbonyl carbon, is an alkyl group having 8 to 18 carbon atoms, and $R^{18}$ and $R^{19}$ are independently selected from hydrogen or an alkyl group having from 1 to about 12 carbon atoms which may or may not be substituted with groups selected from ester groups, ether groups, amine groups, hydroxyl groups, carboxyl groups, carboxyl salts, sulfonate groups, sulfonate salts, and mixtures thereof.

$R^{17}$ can be derived from saturated and unsaturated fatty acid compounds. Suitable compounds include, $C_8$-$C_{18}$ fatty acids, and preferably, the fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic.

Preferred unsaturated fatty acids are those having one or two cis-type double bonds and mixtures of these materials. Suitable materials include myrystoleic, palmitoleic, linolenic and mixtures thereof.

The $R^{18}$ and $R^{19}$ moieties can be the same or different and each being selected from hydrogen and an alkyl group having a carbon chain having from 1 to about 12 carbon atoms. The $R^{18}$ and $R^{19}$ alkyl groups can be straight or branched and can be saturated or unsaturated. When $R^{18}$ and/or $R^{19}$ are an alkyl moiety having a carbon chain of at least 2 carbons, the alkyl group can include one or more substituent groups selected from ester, ether, amine, hydroxyl, carboxyl, carboxyl salts, sulfonate and sulfonate salts. The salts can have one or more cations selected from sodium, potassium or both.

Preferred amide compounds for use in combination with the inhibitory aromatic compounds described herein include sodium lauryl sarcosinate, lauramide monoethanolamide, lauramide diethanolamide, lauramidopropyl dimethylamine, disodium lauramido monoethanolamide sulfosuccinate and disodium lauroamphodiacetate.

In accordance with the present invention, the non-absorbent article contains an effective amount of the combination of the inhibitory aromatic and amide-containing compounds. The amount of amide-containing compound included in the non-absorbent article is at least about 0.0001 millimoles of nitrogen containing compound per gram of non-absorbent article, and desirably at least about 0.005 millimoles of nitrogen containing compound per gram of non-absorbent article. In a preferred embodiment, the non-absorbent article contains from about 0.005 millimoles per gram of non-absorbent article to about 2 millimoles per gram of non-absorbent article.

The non-absorbent articles of the present invention containing a combination of inhibitory or active ingredients such as aromatic inhibitory compounds and amide-containing inhibitory compounds can be a variety of non-absorbent articles including, for example, incontinence devices, barrier birth control devices, contraceptive sponges, douches, tampon applicators, and the like.

The non-absorbent articles of the present invention containing a first inhibitory aromatic compound and a second inhibitory amide-containing compound contain a sufficient amount of both inhibitory compounds to substantially inhibit the formation of TSST-1 when the non-absorbent article is exposed to *S. aureus* bacteria. Desirably, the combination of inhibitory compounds reduces the formation of TSST-1 when the non-absorbent article is exposed to *S. aureus* by at least about 40%, more desirably at least about 50%, still more desirably at least about 60%, still more desirably by at least about 70%, still more desirably by at least about 80%, still more desirably by at least about 90%, and still more desirably by at least about 95%.

The non-absorbent articles of the present invention containing the combination of aromatic inhibitory compounds and amide-containing inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

Typically, the non-absorbent article will contain a molar ratio of inhibitory aromatic compound to amide-containing compound of from about 1:2 to about 1:0.05.

In another embodiment, the inhibitory compounds described herein can be used in combination with amine compounds having the general formula:

$$R^{20}-\underset{\underset{R^{22}}{|}}{\overset{\overset{R^{21}}{|}}{N}}-R^{22}$$

wherein $R^{20}$ is an alkyl group having from about 8 to about 18 carbon atoms and $R^{21}$ and $R^{22}$ are independently selected from the group consisting of hydrogen and alkyl groups having from 1 to about 18 carbon atoms and which can have one or more substitutional moieties selected from the group consisting of hydroxyl, carboxyl, carboxyl salts and imidazoline The combination of aromatic compounds and amine compounds are effective in substantially inhibiting the production of exoprotein from Gram positive bacteria.

Desirably, $R^{20}$ is derived from fatty acid compounds which include, without limitation, caprylic, capric, lauric, myristic, palmitic and stearic acid whose carbon chain lengths are 8, 10, 12, 14, 16, and 18, respectively. Highly preferred materials include capric, lauric, and myristic. Preferred unsaturated fatty acids are those having one or two cis-type double bonds and mixtures of these materials. Suitable materials include myrystoleic, palmitoleic, linolenic, and mixtures thereof.

The $R^{21}$ and $R^{22}$ alkyl groups can further include one or more substitutional moieties selected from hydroxyl, carboxyl, carboxyl salts, and $R^1$ and $R^2$ can form an unsaturated heterocyclic ring that contains a nitrogen that connects via a double bond to the alpha carbon of the $R^1$ moiety to form a substituted imidazoline. The carboxyl salts can have one or more cations selected from sodium potassium or both. The $R^{20}$, $R^{21}$, and $R^{22}$ alkyl groups can be straight or branched and can be saturated or unsaturated.

Preferred amine compounds for use with the aromatic compounds described herein include triethanolamide laureth sulfate, lauramine, lauramino propionic acid, sodium lauriminodipropionic acid, lauryl hydroxyethyl imidazonline and mixtures thereof.

In another embodiment, the amine compound can be an amine salt having the general formula:

$$R^{23}-\underset{\underset{R^{26}}{|}}{\overset{\overset{R^{24}}{|}}{N^+}}-R^{25}$$

wherein $R^{23}$ is an anionic moiety associated with the amine and is derived from an alkyl group having from about 8 to about 18 carbon atoms, and $R^{24}$, $R^{25}$, and $R^{26}$ are independently selected from the group consisting of hydrogen and alkyl group having from 1 to about 18 carbon atoms and which can have one or more substitutional moieties selected from the group consisting of hydroxyl, carboxyl, carboxyl salts, and imidazoline. $R^{24}$, $R^{25}$, and $R^{26}$ can be saturated or unsaturated. Desirably, $R^{23}$ is a polyalkyloxylated alkyl sulfate. A preferred compound illustrative of an amine salt is triethanolamide laureth sulfate.

In accordance with the present invention, the non-absorbent article contains an effective amount of the combination of the inhibitory aromatic and amine and/or amine salt compounds. The amount of amine and/or amine salt compound included in the non-absorbent article is at least about 0.0001 millimoles of ether per gram of non-absorbent article, and desirably at least about 0.005 millimoles of ether per gram of non-absorbent article. In a preferred embodiment, the non-absorbent article contains from about 0.005 millimoles per gram of non-absorbent article to about 2 millimoles per gram of non-absorbent article.

The non-absorbent articles of the present invention containing a combination of two active ingredients can be a variety of non-absorbent articles including, for example, incontinence devices, barrier birth control devices, contraceptive sponges, douches, tampon applicators, and the like.

The non-absorbent articles of the present invention containing a first inhibitory aromatic compound and a second inhibitory amine and/or amine salt compound contain a sufficient amount of both inhibitory compounds to substantially inhibit the formation of TSST-1 when the non-absorbent article is exposed to *S. aureus* bacteria. Desirably, the combination of inhibitory compounds reduces the formation of TSST-1 when the non-absorbent article is exposed to *S. aureus* by at least about 40%, more desirably at least about 50%, still more desirably at least about 60%, still more desirably by at least about 70%, still more desirably by at least about 80%, still more desirably by at least about 90%, and still more desirably by at least about 95%.

The non-absorbent articles of the present invention containing the combination of aromatic inhibitory compounds and amine and/or amine salt inhibitory compounds may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents.

Typically, the non-absorbent article will contain a molar ratio of inhibitory aromatic compound to amine and/or amine salt compound of from about 1:2 to about 1:0.05.

The present invention is illustrated by the following examples which are merely for the purpose of illustration and are not to be regarded as limiting the scope of the invention or manner in which it may be practiced.

EXAMPLE 1

In this Example, the effect of various test compounds on the growth of S. aureus and the production of TSST-1 was determined. The test compound, in the desired concentration (expressed in percent of active compound) was placed in 10 mL of a growth medium in a sterile, 50 mL conical polypropylene tube (Sarstedt, Inc. Newton, N.C.).

The growth medium was prepared by dissolving 37 grams of brain heart infusion broth (BHI) (Difco Laboratories, Cockeysville, Md.) in 880 mL of distilled water and sterilizing the broth according to the manufacturer's instructions. The BHI was supplemented with fetal bovine serum (FBS) (100 mL) (Sigma Chemical Company, St. Louis, Mo.). Hexahydrate of magnesium chloride (0.021 M, 10 mL) (Sigma Chemical Company, St. Louis, Mo.) was added to the BHI-FBS mixture. Finally, L-glutamine (0.027 M, 10 mL) (Sigma Chemical Company, St. Louis, Mo.) was added to the mixture.

Compounds to be tested included phenylethyl alcohol, benzyl alcohol, and 2-hydroxybenzamide. Test compounds were both liquids and solids. The liquid test compounds were added directly to the growth medium and diluted in growth medium to obtain the desired final concentrations. The solid test concentrations were dissolved in methanol, spectrophotometric grade (Sigma Chemical Company, St. Louis, Mo.) at a concentration that permitted the addition of 200 microliters of the solution to 10 mL of growth medium for the highest concentration tested. Each test compound that was dissolved in methanol was added to the growth medium in the amount necessary to obtain the desired final concentration.

In preparation for inoculation of the tubes of growth medium containing the test compounds, an inoculating broth was prepared as follows: *S. aureus* (MN8) was streaked onto a tryptic soy agar plate (TSA; Difco Laboratories Cockeysville, Md.) and incubated at 35° C. The test organism was obtained from Dr. Pat Schlievert, Department of Microbiology, University of Minnesota Medical School, Minneapolis, Minn. After 24 hours of incubation three to five individual colonies were picked with a sterile inoculating loop and used to inoculate 10 mL of growth medium. The tube of inoculated growth medium was incubated at 35° C. in atmospheric air. After 24 hours of incubation, the culture was removed from the incubator and mixed well on a S/P brand vortex mixer. A second tube containing 10 mL of the growth medium was inoculated with 0.5 mL of the above-described 24 hour old culture and incubated at 35° C. in atmospheric air. After 24 hours of incubation the culture was removed from the incubator and mixed well on a S/P brand vortex mixer. The optical density of the culture fluid was determined in a microplate reader (Bio-Tek Instruments, Model EL309, Winooski, Vt.). The amount of inoculum necessary to give $5 \times 10^6$ CFU/mL in 10 mL of growth medium was determined using a standard curve.

This Example included tubes of growth medium with varying concentrations of test compounds, tubes of growth medium without test compounds (control) and tubes of growth medium with 20-400 microliters of methanol (control). Each tube was inoculated with the amount of inoculum determined as described above. The tubes were capped with foam plugs (Identi-plug plastic foam plugs, Jaece Industries purchased from VWR Scientific Products, South Plainfield, N.J.). The tubes were incubated at 35° C. in atmospheric air containing 5% by volume $CO_2$. After 24 hours of incubation the tubes were removed from the incubator and the optical density (600 nm) of the culture fluid was determined and the culture fluid was assayed for the number of colony forming units of *S. aureus* and was prepared for the analysis of TSST-1 as described below.

The number of colony forming units per mL after incubation was determined by standard plate count procedures. In preparation for analysis of TSST-1, the culture fluid broth was centrifuged and the supernatant subsequently filter sterilized through an Autovial 5 syringeless filter, 0.2 micrometers pore size (Whatman, Inc., Clifton, N.J.). The resulting fluid was frozen at −70° C. until assayed.

The amount of TSST-1 per mL was determined by a non-competitive, sandwich enzyme-linked immunonon-absorbent assay (ELISA). Samples of the culture fluid and the TSST-1 reference standard were assayed in triplicate. The method employed was as follows: four reagents, TSST-1 (#TT-606), rabbit polyclonal anti-TSST-1 IgG (LTI-101), rabbit polyclonal anti-TSST-1 IgG conjugated to horseradish peroxidase (LTC-101), and normal rabbit serum (NRS) certified anti-TSST-1 free (NRS-10) were purchased from Toxin Technology (Sarasota, Fla.). A 10 microgram/millimeter solution of the polyclonal rabbit anti-TSST-1 IgG was prepared in phosphate buffered saline (PBS) (pH 7.4). The PBS was prepared from 0.016 molar $NaH_2PO_4$, 0.004 molar $NaH_2PO_4$-$H_2O$, 0.003 molar KCl and 0.137 molar NaCl, (Sigma Chemical Company, St. Louis, Mo.). One hundred microliters of the polyclonal rabbit anti-TSST-1 IgG solution was pipetted into the inner wells of polystyrene microplates (Nunc-Denmark, Catalogue Number 439454). The plates were covered and incubated at room temperature overnight. Unbound anti-toxin was removed by draining until dry. TSST-1 was diluted to 10 nanograms/milliliter in PBS with phosphate buffered saline (pH7.4) containing 0.05% (vol/vol) Tween-20 (PBS-Tween) (Sigma Chemical Company, St. Louis, Mo.) and 1% NRS (vol/vol) and incubated at 4° C. overnight. Test samples were combined with 1% NRS (vol/vol) and incubated at 4° C. overnight. The plates were treated with 100 microliters of a 1% solution of the sodium salt of casein in PBS (Sigma Chemical Company, St. Louis, Mo.), covered and incubated at 35° C. for one hour. Unbound BSA was removed by 3 washes with PBS-Tween. TSST-1 reference standard (10 nanograms/milliliter) treated with NRS, test samples treated with NRS, and reagent controls were pipetted in 200 microliter volumes to their respective wells on the first and seventh columns of the plate. One hundred microliters of PBS-Tween was added to the remaining wells. The TSST-1 reference standard and test samples were then serially diluted 6 times in the PBS-Tween by transferring 100 microliters from well-to-well. The samples were mixed prior to transfer by repeated aspiration and expression. This was followed by incubation for 1.5 hours at 35° C. and five washes with PBS-T and three washes with distilled water to remove unbound toxin. The rabbit polyclonal anti-TSST-1 IgG conjugated to horseradish peroxidase wash diluted according to manufacturer's instructions and 50 microliters was added to each microtiter well, except well A-1, the conjugate control well. The plates were covered and incubated at 35° C. for one hour.

Following incubation the plates were washed five times in PBS-Tween and three times with distilled water. Following the washes, the wells were treated with 100 microliters of horseradish peroxidase substrate buffer consisting of 5 milligrams of o-phenylenediamine and 5 microliters of 30% hydrogen peroxide in 11 mL of citrate buffer (pH 5.5). The citrate buffer was prepared from 0.012 M anhydrous citric acid and 0.026 molar dibasic sodium phosphate. The plates were incubated for 15 minutes at 35° C. The reaction was stopped by the addition of 50 microliters of a 5% sulfuric acid solution. The intensity of the color reaction in each well was evaluated using the BioTek Model EL309 microplate reader (OD 490 nanometers). TSST-1 concentrations in the test samples were determined from the reference toxin regression equation derived during each assay procedure. The efficacy of the compound in inhibiting the production of TSST-1 is shown in Table I below.

In accordance with the present invention, the data in Table 1 shows that S. aureus (MN8), when compared to the control, produced significantly less TSST-1 in the presence of the aromatic compounds. The aromatic compounds reduced the amount of exotoxin production ranging from about 91% to about 96%. However, although the amount of toxin produced was significantly reduced, there was minimal, if any, effect on the growth of *S. aureus* cells.

TABLE 1

| Compound | % Test Compound | Optical Density | CFU/mL | ELISA: TSST-1 ng/OD unit | Reduction of Toxin (%) |
|---|---|---|---|---|---|
| Growth Medium | Zero | 0.625 | 2.8E+08 | 1504 | N/A |
| Methanol | 400 μL | 0.627 | 2.8E+08 | 1440 | N/A |
| Phenylethyl alcohol | 0.5% | 0.542 | 1.6E+08 | 60 | 96% |
| Benzyl alcohol | 0.5% | 0.792 | 1.8E+08 | 131 | 91% |
| 2-hydroxy-benzamide | 1.0% | 0.549 | 9.0E+07 | 65 | 95% |

N/A = Not Applicable

EXAMPLE 2

In this Example, the effect of various test compounds on the growth of *S. aureus* and the production of TSST-1 was determined. The effect of the test compounds tested in Example 2 was determined by placing the desired concentration, expressed in percent of the active compound, in 10 mL of a growth medium as described in Example 1. The test compounds were then tested and evaluated as in Example 1.

In accordance with the present invention, Table 2 shows that *S. aureus* (MN8), when compared to the control, produced significantly less TSST-1 in the presence of the aromatic compounds. The aromatic compounds reduced the amount of exotoxin production ranging from about 82% to 97%. However, although the amount of toxin produced was significantly reduced, there was minimal, if any, effect on the growth of *S. aureus* cells.

TABLE 2

| Compound | % Test Compound | Optical Density | CFU/mL | ELISA: TSST-1 ng/OD unit | Reduction of Toxin % |
|---|---|---|---|---|---|
| Growth Medium | Zero | 0.607 | >1.6E+09 | 2424 | N/A |
| Methanol | 400 μL | 0.598 | 2.6E+09 | 2690 | N/A |
| Phenylethyl alcohol | 0.5% | 0.551 | 4.2E+08 | 68 | 97% |

TABLE 2-continued

| Compound | % Test Compound | Optical Density | CFU/mL | ELISA: TSST-1 ng/OD unit | Reduction of Toxin % |
|---|---|---|---|---|---|
| Phenoxy-ethanol | 0.6% | 0.681 | 8.3E+08 | 70 | 97% |
| Phenoxy-ethanol | 0.5% | 0.728 | >1.7E+09 | 122 | 95% |
| p-hydroxy-benzoic acid, methyl ester | 0.2% | 0.356 | >1.5E+08 | 506 | 82% |
| 2-hydroxy-benzoic acid | 0.2% | 0.682 | 1.48E+09 | 193 | 93% |
| p-amino-benzoic acid | 0.2% | 0.618 | 1.1E+09 | 317 | 89% |

N/A = Not Applicable

EXAMPLE 3

In this Example, the effect of various test compounds on the growth of *S. aureus* and the production of TSST-1 was determined. The effect of the test compounds tested in Example 3 was determined by placing the desired concentration, expressed in percent of the active compound, in 10 mL of a growth medium as described in Example 1. The test compounds were then tested and evaluated as in Example 1.

In accordance with the present invention, Table 3 shows that *S. aureus* (MN8), when compared to the control, produced significantly less TSST-1 in the presence of the aromatic compounds. The aromatic compounds reduced the amount of exotoxin production ranging from about 69% to 98%. However, although the amount of toxin produced was significantly reduced, there was minimal, if any, effect on the growth of *S. aureus* cells.

TABLE 3

| Compound | % Test Compound | Optical Density | CFU/mL | ELISA: TSST-1 ng/OD unit | Reduction of Toxin % |
|---|---|---|---|---|---|
| Growth Medium | Zero | 0.627 | 3.9E+09 | 1931 | N/A |
| Methanol | 100 uL | 0.588 | 5.2E+09 | 2041 | N/A |
| Phenylethyl alcohol | 0.5% | 0.476 | 5.5E+08 | 46 | 98% |
| Trans-cinnamic acid | 0.5% | 0.549 | 1.7E+09 | 436 | 82% |
| Acetyl tyrosine | 0.5% | 0.549 | 1.7E+09 | 436 | 69% |
| Gallic acid | 0.5% | 0.492 | 1.2E+09 | 63 | 95% |

N/A = Not Applicable

EXAMPLE 4

In this Example, the effect of various test compounds on the growth of *S. aureus* and the production of TSST-1 was determined. The effect of the test compounds tested in Example 4 was determined by placing the desired concentration, expressed in percent of the active compound, in 10 mL of a growth medium as described in Example 1. The test compounds were then tested and evaluated as in Example 1.

In accordance with the present invention, Table 4 shows that *S. aureus* (MN8), when compared to the control, produced significantly less TSST-1 in the presence of the aromatic compounds. The aromatic compounds reduced the amount of exotoxin production ranging from about 79% to 98%. However, although the amount of toxin produced was significantly reduced, there was minimal, if any, effect on the growth of S. aureus cells.

TABLE 4

| Compound | % Test Compound | Optical Density | CFU/mL | ELISA: TSST-1 ng/OD unit | Reduction of Toxin % |
|---|---|---|---|---|---|
| Growth Medium | Zero | 0.606 | 3.2E+09 | 1445 | N/A |
| Methanol | 100 µL | 0.567 | 1.3E+09 | 1151 | N/A |
| Phenylethyl alcohol | 0.5% | 0.554 | 5.4E+08 | 25 | 98% |
| 4-Acetamido-phenol | 0.5% | 0.629 | 2.4E+09 | 230 | 79% |

N/A = Not Applicable

EXAMPLE 5

In this Example the growth of S. aureus and the production of TSST-1 in the presence of phenylethyl alcohol was measured using different TSST-1 producing strains of S. aureus. S. aureus FRI-1187 and FRI-1169 were obtained as lyophilized cultures from the stock collection of Dr. Merlin Bergdoll, Food Research Institute (Madison Wis.). The effect of the phenylethyl alcohol was determined by placing the desired concentration, expressed in percent of the active compound, in 10 mL of a growth medium as in Example 1. The phenylethyl alcohol was then tested and evaluated as in Example 1.

In accordance with the present invention, Table 5 shows that S. aureus when compared to the control, produced significantly less TSST-1 in the presence of the phenylethyl alcohol. The phenylethyl alcohol reduced the amount of exotoxin production from the FRI-1169 culture from about 95% to about 100%. The phenylethyl alcohol also significantly reduced the amount of exotoxin production from the FRI-1187 culture. However, although the amount of toxin produced was significantly reduced, there was minimal, if any, effect on the growth of S. aureus cells.

TABLE 5

| Compound | % Test Compound | Optical Density | CFU/mL | ELISA: TSST-1 ng/OD unit | Reduction of Toxin % |
|---|---|---|---|---|---|
| S. aureus FRI-11698 | | | | | |
| Growth medium | Zero | 1.068 | 1.11e+09 | 158 | N/A |
| Phenylethyl alcohol | 0.5% | 1.263 | 3.03E+08 | 2 | 99% |
| Phenylethyl alcohol | 0.25% | 1.208 | 2.05E+09 | 8 | 95% |
| S. aureus FRI-1187 | | | | | |
| Growth medium | Zero | 1.056 | 1.59E+09 | 92 | N/A |
| Phenylethyl alcohol | 0.5% | 1.296 | 2.55E+08 | none detected | 100% |

TABLE 5-continued

| Compound | % Test Compound | Optical Density | CFU/mL | ELISA: TSST-1 ng/OD unit | Reduction of Toxin % |
|---|---|---|---|---|---|
| Phenylethyl alcohol | 0.25% | 1.244 | 1.80E+09 | 1 | 98% |

N/A = Not Applicable

EXAMPLE 6

In this Example, the effect of test compounds in combination with surface active agents was evaluated utilizing a checkerboard experimental design. This allowed the evaluation of the interaction of two test compounds on the growth of S. aureus and the production of TSST-1. Four concentrations of one test compound (including zero) were combined with five concentrations of a second test compound (including zero) in test tubes. In this Example, phenyethyl alcohol (0%, 0.5%, 0.3%, 0.15%, and 0.05%) was combined with Cetiol 1414E (myreth-3 myristate) (10 mM, 5 mM, 2.5 mM and 0). The test solutions were otherwise prepared as described in Example 1 and evaluated in the same manner as Example 1.

As Table 6 below indicates, at every concentration of Cetiol 1414E, the phenylethyl alcohol increased the inhibition of production of TSST-1, and vice versa. The effect appears to be additive.

TABLE 6

| Cetiol 1414E | PEA (%) | ng TSST-1/mL | CFU/mL | Log CFU/mL | ng TSST-1 per CFU | Reduction of Toxin % |
|---|---|---|---|---|---|---|
| 0 | 0.5 | 106 | 3.95E+08 | 8.6 | 27 | 93% |
| 0 | 0.3 | 201 | 5.15E+08 | 8.7 | 39 | 90% |
| 0 | 0.15 | 561 | 4.35E+08 | 8.6 | 129 | 67% |
| 0 | 0.05 | 826 | 3.10E+08 | 8.5 | 266 | 32% |
| 0 | 0 | 1178 | 3.00E+08 | 8.5 | 393 | 0% |
| 10 mM | 0.5 | 20 | 4.70E+08 | 8.7 | 4 | 99% |
| 10 mM | 0.3 | 59 | 7.20E+08 | 8.9 | 8 | 98% |
| 10 mM | 0.15 | 137 | 4.30E+08 | 8.6 | 32 | 92% |
| 10 mM | 0.05 | 240 | 4.60E+08 | 8.7 | 52 | 87% |
| 10 mM | 0 | 262 | 4.30E+08 | 8.6 | 61 | 84% |
| 5 mM | 0.5 | 58 | 6.25E+08 | 8.8 | 9 | 98% |
| 5 mM | 0.3 | 155 | 4.00E+08 | 8.6 | 39 | 90% |
| 5 mM | 0.15 | 348 | 4.10E+08 | 8.6 | 85 | 78% |
| 5 mM | 0.05 | 538 | 4.75E+08 | 8.7 | 113 | 71% |
| 5 mM | 0 | 558 | 3.25E+08 | 8.5 | 172 | 56% |
| 2.5 mM | 0.5 | 76 | 6.90E+08 | 8.8 | 11 | 97% |
| 2.5 mM | 0.3 | 197 | 2.80E+08 | 8.4 | 70 | 82% |
| 2.5 mM | 0.15 | 384 | 4.95E+08 | 8.7 | 78 | 80% |
| 2.5 mM | 0.05 | 618 | 4.15E+08 | 8.6 | 149 | 62% |
| 2.5 mM | 0 | 765 | 3.20E+08 | 8.5 | 239 | 39% |

EXAMPLE 7

In this Example, the effect of phenylethyl alcohol and 4-hydroxybenzoic acid, methyl ester on the production of alpha-toxin from S. aureus strain RN 6390 was evaluated utilizing a standard hemolytic assay.

The S. aureus alpha-toxin is a hemolytic exoprotein that causes target cell membrane damage and cell death. It is produced under environmental conditions similar to those seen with TSST-1 production. The effect of the test compounds on the growth of S. aureus and the production of alpha-toxin was carried out by placing the desired concentrations, expressed in percent of the active compound, in 100 mL of growth medium in 500 mL fleakers capped with aluminum foil. The growth medium and inoculum were prepared as described in Example 1. The fleakers were incubated in a 37° C. water bath with a gyratory shaker set at 180 rpm. Growth was followed by periodic optical density measurements at 600 nm. When the growth obtained an optical density of 1.0, 10 mL aliquots were removed for analysis. Plate counts were performed on the aliquots to determine cell count and culture purity. The remaining culture fluid was centrifuged at 2500 rpm for 15 minutes and the resulting supernatant filter sterilized and frozen at −70° C. until assayed.

Defibrinated rabbit red blood cells (Hema Resources, Aurora, Oreg.) were washed 3 times in Tris-saline buffer and re-suspended to a concentration of 0.5% (volume/volume). The Tris-saline buffer consisted of 50 mM Trizma® hydrochloride/Trizma base and 100 mM sodium chloride, with a final pH of 7.0. Culture supernatants were serially diluted in Tris-saline buffer from 1:2 to 1:256. One hundred microliters of each dilution was added to nine hundred microliters of the rabbit red blood cells. Each dilution was set up in triplicate. The tubes were incubated for 30 minutes at 37° C. The samples were then centrifuged at 800×g for 6 minutes. Two two-hundred microliter aliquots of each tube were transferred to a microtiter plate and the optical density determined at 410 nm. Control fluids used in place of the culture supernatants included tris-saline buffer (zero lysis), 10% sodium dodecyl sulfate (100% lysis), and sterile growth medium containing the test compound. Units of activity are expressed as the reciprocal of the dilution of each test sample giving 50% lysis in samples that were adjusted to the same initial optical density. As Tables 7 and 8 below indicate both phenylethyl alcohol and 4-hydroxybenzoic acid methyl ester significantly reduced production of the alpha toxin.

TABLE 7

| Test Compound | % Test Compound | Hemolytic Endpoint 50% lysis | % Toxin Inhibition |
|---|---|---|---|
| None | 0 | 103 | N/A |
| Phenylethyl alcohol | 0.3% | 3 | 97% |
| Phenylethyl alcohol | 0.4% | None Detected | 100% |

N/A = Not Applicable

TABLE 8

| Test Compound | % Test Compound | Hemolytic Endpoint 50% lysis | % Toxin Inhibition |
|---|---|---|---|
| None | 0 | 265 | N/A |
| 4-hydroxybenzoic acid methyl ester | 0.1% | 79 | 70% |
| 4-hydroxybenzoic acid methyl ester | 0.2% | 16 | 94% |

N/A = Not Applicable

EXAMPLE 8

In this Example, the effect of phenylethyl alcohol in combination with Glucopon was evaluated utilizing a checkerboard experimental design. This allowed the evaluation of the interaction of two test compounds on the growth of $S.$ $aureus$ and the production of TSST-1.

Five concentrations of phenylethyl alcohol (0.5%, 0.3%, 0.15%, 0.05%, and 0.0%) were combined with four concentrations of Glucopon (1.5 mM, 0.75 mM, 0.25 mM and 0 mM) in a twenty tube array. For example, tube #1 contained 0 mM of Glucopon and 0.5% phenylethyl alcohol (vol/vol) in 10 mL of growth medium (as prepared in Example 1). Each of tubes #1-#20 contained a unique combination of Glucopon and phenylethyl alcohol. These combinations were tested and evaluated as in Example 1. The effect of the test compounds on the growth of $S.$ $aureus$ and on the production of TSST-1 is shown in Table 9 below.

TABLE 9

| Glucopon | PEA (%) | OD | ng TSST-1/OD | CFU/mL | % Reduction |
|---|---|---|---|---|---|
| 0 mM | 0.0 | 0.685 | 755 | 9.05E+08 | N/A |
| 0 mM | 0.05 | 0.712 | 323 | 1.07E+09 | 57% |
| 0 mM | 0.15 | 0.730 | 152 | 2.59E+09 | 80% |
| 0 mM | 0.3 | 0.758 | 54 | 1.97E+09 | 93% |
| 0 mM | 0.50 | 0.721 | 13 | 2.15E+09 | 98% |
| 0.25 mM | 0.0 | 0.660 | 542 | 1.26E+09 | 28% |
| 0.25 mM | 0.05 | 0.690 | 351 | 2.05E+09 | 54% |
| 0.25 mM | 0.15 | 0.705 | 173 | 2.44E+09 | 77% |
| 0.25 mM | 0.3 | 0.797 | 48 | 2.20e+09 | 94% |
| 0.25 mM | 0.5 | 0.657 | 14 | 1.21E+09 | 98% |
| 0.75 mM | 0.0 | 0.701 | 599 | 9.55E+08 | 21% |
| 0.75 mM | 0.05 | 0.705 | 285 | 8.60E+08 | 62% |
| 0.75 mM | 0.15 | 0.743 | 148 | 9.75E+08 | 80% |
| 0.75 mM | 0.3 | 0.731 | 45 | 2.19E+09 | 94% |
| 0.75 mM | 0.5 | 0.099 | 0 | 4.51E+07 | 100% |
| 1.5 mM | 0.0 | 0.718 | 196 | 1.83E+09 | 74% |
| 1.5 mM | 0.05 | 0.730 | 132 | 1.97E+09 | 83% |
| 1.5 mM | 0.15 | 0.694 | 68 | 1.11E+09 | 91% |
| 1.5 mM | 0.3 | 0.390 | 28 | >5.00E+07 | 96% |
| 1.5 mM | 0.5 | 0.014 | 0 | no growth | N/A |

N/A = Not Applicable

As Table 9 below indicates, at every concentration of GLUCOPON the phenylethyl alcohol increased the inhibition of production of TSST-1, and vice versa. The effect appears to be additive.

EXAMPLE 10

In this Example, the effect of Cetiol in combination with para-aminobenzoic acid was evaluated utilizing a checkerboard experimental design. This allowed the evaluation of the interaction of two test compounds on the growth of $S.$ $aureus$ and the production of TSST-1.

Five concentrations of para-aminobenzoic acid (0.05%, 0.09%, 0.19%, 0.38%, and 0.0%) were combined with four concentrations of Cetiol (2.5 mM, 5 mM, 10 mM and 0 mM) in a twenty tube array. For example, tube #1 contained 0% of para-aminobenzoic acid and 0 mM Cetiol (vol/vol) in 10 mL of growth medium (as prepared in Example 1). Each of tubes #1-#20 contained a unique combination of Cetiol and para-aminobenzoic acid. These combinations were tested and evaluated as in Example 1. The effect of the test compounds on the growth of $S.$ $aureus$ and on the production of TSST-1 is shown in Table 10 below.

TABLE 10

| Cetiol | PABA | OD | ng TSST-1/OD | CFU/mL | % Reduction |
|---|---|---|---|---|---|
| 0 mM | 0% | 0.517 | 4907 | 8.90E+08 | N/A |
| 0 mM | 0.05% | 0.546 | 5670 | 1.53E+09 | 0% |
| 0 mM | 0.09% | 0.558 | 3389 | 1.85E+09 | 31% |
| 0 mM | 0.19% | 0.599 | 1975 | 1.79E+09 | 60% |
| 0 mM | 0.38% | 0.589 | 1039 | 1.15E+09 | 79% |
| 2.5 mM | 0% | 0.637 | 3367 | 1.21E+09 | 31% |
| 2.5 mM | 0.05% | 0.632 | 2193 | 1.89E+09 | 55% |
| 2.5 mM | 0.09% | 0.616 | 2413 | 1.46E+09 | 51% |
| 2.5 mM | 0.19% | 0.611 | 2106 | 1.38E+09 | 57% |
| 2.5 mM | 0.38% | 0.612 | 891 | 1.31E+09 | 82% |
| 5 mM | 0% | 0.881 | 2419 | 8.25E+08 | 51% |
| 5 mM | 0.05% | 0.957 | 1942 | 4.75E+08 | 60% |
| 5 mM | 0.09% | 0.862 | 1875 | 8.25E+08 | 62% |
| 5 mM | 0.19% | 0.849 | 1048 | 8.90E+08 | 79% |
| 5 mM | 0.38% | 0.971 | 221 | 1.19E+09 | 95% |
| 10 mM | 0% | 0.976 | 2286 | 3.95E+08 | 53% |
| 10 mM | 0.05% | 1.317 | 1420 | 4.80E+08 | 71% |
| 10 mM | 0.09% | 1.266 | 1244 | 8.10E+08 | 75% |
| 10 mM | 0.19% | 0.806 | 674 | 6.00E+08 | 86% |
| 10 mM | 0.38% | 0.749 | 467 | 6.55E+08 | 90% |

N/A = Not Applicable

In view of the above, it will be seen that the several objects of the invention are achieved. As various changes could be made in the above-described non-absorbent articles without departing from the scope of the invention, it is intended that all matter contained in the above description be interpreted as illustrative and not in a limiting sense.

What is claimed is:

1. An exoprotein inhibitor for inhibiting the production of exoproteins from Gram positive bacteria in and around the vagina comprising a non-absorbent substrate for insertion into a vagina being selected from the group consisting of a non-absorbent incontinence device, a barrier birth control device, a tampon applicator, and a douche, the non-absorbent substrate having deposited thereon an effective amount of a first active ingredient, an effective amount of a second active ingredient, and a pharmaceutically active material selected from the group consisting of antimicrobials, antioxidants, anti-parasitic agents, antipruritics, astringents, local anaesthetics, and anti-inflammatory agents, the first active ingredient having the general formula:

wherein $R^1$ is selected from the group consisting of H, —C(O)$NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —C(O)$R^9$; $R^9$ is hydrogen or a monovalent saturated or unsaturated aliphatic hydrocarbyl moiety, the second active ingredient having the general formula:

$R^{10}$—O—$R^{11}$ wherein $R^{10}$ is a straight or branched alkyl or straight or branched alkenyl having from 8 to about 18 carbon atoms and $R^{11}$ is selected from the group consisting of an alcohol, a polyalkoxylated sulfosuccinate salt, and wherein the first active ingredient and the second active ingredient are effective in inhibiting the production of exoprotein from Gram positive bacteria.

2. An exoprotein inhibitor for inhibiting the production of exoproteins from Gram positive bacteria in and around the vagina comprising a non-absorbent substrate for insertion into a vagina being selected from the group consisting of a non-absorbent incontinence device, a barrier birth control device, a tampon applicator, and a douche, the non-absorbent substrate having deposited thereon an effective amount of a first active ingredient and an effective amount of a second active ingredient, the first active ingredient having the general formula:

wherein $R^1$ is selected from the group consisting of H, —C(O)$NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —C(O)$R^9$; $R^9$ is hydrogen or a monovalent saturated or unsaturated aliphatic hydrocarbyl moiety, wherein the first active ingredient is effective in inhibiting the production of exoprotein from Gram positive bacteria, and the second active ingredient comprising an alkyl polyglycoside effective in substantially inhibiting the production of exoprotein from Gram positive bacteria.

3. The exoprotein inhibitor as set forth in claim 2 wherein the alkyl polyglycoside has an alkyl group having from about 8 to about 18 carbon atoms.

4. The exoprotein inhibitor as set forth in claim 3 wherein the alkyl group is a linear alkyl group.

5. The exoprotein inhibitor as set forth in claim 3 wherein the alkyl polyglycoside has an alkyl group having from about 8 to about 14 carbon atoms.

6. The exoprotein inhibitor as set forth in claim 2 wherein the alkyl polyglycoside has an HLB of 12 to 14.

7. The exoprotein inhibitor as set forth in claim 2 wherein the alkyl polyglycoside has an HLB of 10 to 15.

8. The exoprotein inhibitor as set forth in claim 2 wherein the alkyl polyglycoside has the general formula:

H—($Z_n$)—O—$R^{14}$ wherein Z is a saccharide residue having 5 or 6 carbon atoms, n is a whole number from 1 to 6, and $R^{14}$ is a linear alkyl group having from about 8 to about 18 carbon atoms.

9. The exoprotein inhibitor as set forth in claim 8 wherein $R^{14}$ is a linear alkyl group having from about 8 to about 14 carbon atoms.

10. The exoprotein inhibitor as set forth in claim 8 wherein $R^{14}$ is a linear alkyl group having from about 8 to about 12 carbon atoms.

11. The exoprotein inhibitor as set forth in claim 2 wherein the second active ingredient is present in an amount of at least about 0.0001 millimoles per gram of non-absorbent substrate.

12. The exoprotein inhibitor as set forth in claim 2 wherein the second active ingredient is present in an amount of at least about 0.005 millimoles per gram of non-absorbent substrate.

13. The exoprotein inhibitor as set forth in claim 2 wherein the second active ingredient is present in an amount of at least about 0.005 millimoles per gram of non-absorbent substrate to about 2 millimoles per gram of non-absorbent substrate.

14. An exoprotein inhibitor for inhibiting the production of exoproteins from Gram positive bacteria in and around the vagina comprising a non-absorbent substrate for insertion into a vagina being selected from the group consisting of a non-absorbent incontinence device, a barrier birth control device, a tampon applicator, and a douche, the non-absorbent substrate having deposited thereon an effective amount of a first active ingredient and an effective amount of a second active ingredient, the first active ingredient having the general formula:

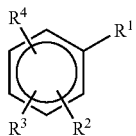

wherein $R^1$ is selected from the group consisting of H, —C(O)NH$_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —C(O)R$^9$; $R^9$ is hydrogen or a monovalent saturated or unsaturated aliphatic hydrocarbyl moiety, wherein the first active ingredient is effective in inhibiting the production of exoprotein from Gram positive bacteria, the second active ingredient being selected from the group consisting of glycerol monolaurate and myreth-3-myristate wherein said second active ingredient is effective in substantially inhibiting the production of exoprotein from Gram positive bacteria.

15. An exoprotein inhibitor for inhibiting the production of exoproteins from Gram positive bacteria in and around the vagina comprising a non-absorbent substrate for insertion into a vagina being selected from the group consisting of a non-absorbent incontinence device, a barrier birth control device, a tampon applicator, and a douche, the non-absorbent substrate having deposited thereon an effective amount of a first active ingredient and an effective amount of a second active ingredient, the first active ingredient having the general formula:

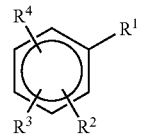

wherein $R^1$ is selected from the group consisting of H, —C(O)NH$_2$ and salts thereof; $R^5$ is a monovalent saturated or unsaturated aliphatic hydrocarbyl moiety; R6 is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —C(O)R$^9$; $R^9$ is hydrogen or a monovalent saturated or unsaturated aliphatic hydrocarbyl moiety, wherein the first active ingredient is effective in inhibiting the production of exoprotein from Gram positive bacteria, and the second active ingredient having the general formula:

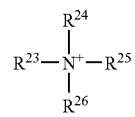

wherein $R^{23}$ is an alkyl group having from 8 to about 18 carbon atoms and $R^{24}$, $R^{25}$, and $R^{26}$ are independently selected from the group consisting of hydrogen and alkyl group having from 1 to about 18 carbon atoms and which can have one or more substitutional moieties selected from the group consisting of hydroxyl, carboxyl, carboxyl salts, and imidazoline wherein the second active ingredient is effective in substantially inhibiting the production of exoprotein from Gram positive bacteria.

16. The exoprotein inhibitor as set forth in claim 15 wherein the second active ingredient is triethanolamide laureth sulfate.

17. The exoprotein inhibitor as set forth in claim 15 wherein the second active ingredient is present in an amount of at least about 0.0001 millimoles per gram of non-absorbent substrate.

18. The exoprotein inhibitor as set forth in claim 15 wherein the second active ingredient is present in an amount of at least about 0.005 millimoles per gram of non-absorbent substrate.

19. The exoprotein inhibitor as set forth in claim 15 wherein the second active ingredient is present in an amount from about 0.005 millimoles per gram of non-absorbent substrate to about 0.2 millimoles per gram of non-absorbent substrate.

20. The exoprotein inhibitor as set forth in claim 15 further comprising a pharmaceutically active material selected from the group consisting of antimicrobials, antioxidants, anti-parasitic agents, antipruritics, astringents, local anaesthetics and anti-inflammatory agents.

* * * * *